US00PP11943P2

(12) United States Plant Patent
Booman

(10) Patent No.: US PP11,943 P2
(45) Date of Patent: Jun. 19, 2001

(54) BEGONIA PLANT NAMED 'OMAHA BEEFSTEAK'

(76) Inventor: James Lawrence Booman, 2302 Bautista Ave., Vista, CA (US) 92084

( * ) Notice: Subject to any disclaimer, the term of this patent is extended or adjusted under 35 U.S.C. 154(b) by 0 days.

(21) Appl. No.: 09/375,785

(22) Filed: Aug. 17, 1999

(51) Int. Cl.[7] ..... A01H 5/00
(52) U.S. Cl. ..... Plt./343

(58) Field of Search ..... Plt./343

*Primary Examiner*—Bruce R. Campell
*Assistant Examiner*—Anne Marie Grünberg
(74) *Attorney, Agent, or Firm*—C. A. Whealy

(57) ABSTRACT

A new and distinct cultivar of Rex Begonia plant named 'Omaha Beefsteak', characterized by its uniform growth habit; moderate plant vigor; no requirement for winter dormancy; and interesting and attractive leaf coloration and pattern.

1 Drawing Sheet

BACKGROUND OF THE INVENTION

The present invention relates to a new and distinct cultivar of Begonia plant, botanically known as *Begonia rex* hybrid, commerically known as Rex Begonia, and hereinafter referred to by the name 'Omaha Beefsteak'.

The new Rex Begonia was discovered and selected by the Inventor in a controlled environment in Vista, Calif., in Aug., 1995, within a large group of seedling progeny from multiple crossings of unidentified selections of *Begonia rex* hybrids.

The selection of this plant was based on its uniform growth habit, moderate plant vigor, and attractive foliage coloration and pattern.

Asexual reproduction of the new Rex Begonia by leaf cuttings taken in a controlled environment in Vista, Calif., has shown that the unique features of this new Rex Begonia are stable and reproduced true to type in successive generations.

SUMMARY OF THE INVENTION

The cultivar 'Omaha Beefsteak' has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Omaha Beefsteak'. These characteristics in combination distinguish 'Omaha Beefsteak' as a new and distinct Rex Begonia:

1. Uniform growth habit.
2. Moderate plant vigor.
3. Does not require winter dormancy.
4. Large leaves.
5. Interesting and attractive leaf coloration and pattern.

In side-by-side comparisons conducted by the Inventor in Vista, Calif., plants of the new Rex Begonia differ from plants of the nonpatented cultivar Merry Christmas Corkscrew in the following characteristics:

1. Plants of the new Rex Begonia grow more rapidly and have larger leaves than plants of the cultivar Merry Christmas Corkscrew.

2. Leaves of plants of the new Rex Begonia and the cultivar Merry Christmas Corkscrew differ in coloration and pattern.
3. Leaves of plants of the new Rex Begonia do not have a "corkscrew" formation whereas leaves of plants of the cultivar Merry Christmas Corkscrew have a "corkscrew" formation.
4. Plants of the new Rex Begonia do not require a winter dormancy period whereas plants of the cultivar Merry Christmas Corkscrew do require a winter dormancy period.

In side-by-side comparisons conducted by the Inventor in Vista, Calif., plants of the new Rex Begonia differ from plants of the nonpatented cultivar Lillium in the following characteristics:

1. Plants of the new Rex Begonia grow more rapidly and have larger leaves than plants of the cultivar Lillium.
2. Leaves of plants of the new Rex Begonia and the cultivar Lillium differ in coloration and pattern.
3. Plants of the new Rex Begonia do not require a winter dormancy period whereas plants of the cultivar Lillium do require a winter dormancy period.

BRIEF DESCRIPTION OF THE PHOTOGRAPH

The accompanying colored photograph illustrates the overall appearance of the new Rex Begonia, showing the colors as true as it is reasonably possible to obtain in colored reproductions of this type. The photograph comprises a top perspective view of a typical plant of 'Omaha Beefsteak'. Foliage colors in the photograph may differ from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown during the Spring in Vista, Calif., under conditions which approximate commercial practice. Plants used for this description were grown in 15-cm containers for about 3 months.

Botanical classification: *Begonia rex* hybrid cultivar Omaha Beefsteak.

Commercial classification: Rex Begonia.

Parentage: Chance seedling of multiple crossings of unidentified selections of *Begonia rex* hybrids.

Propagation:

*Type.*—Leaf cuttings.

*Time to initiate roots, summer.*—About 56 days at 21° C.

*Time to initiate roots, winter.*—About 56 days at 21° C.

*Time to develop roots, summer.*—About 84 days at 21° C.

*Time to develop roots, winter.*—About 98 days at 21° C.

*Rooting habit.*—Fine, fibrous and well-branched.

Plant description:

*Plant form.*—Rosette; compact; dense and outwardly arching potted plant; freely basal branching with good leaf petiole strength.

*Vigor.*—Moderate.

*Plant height, soil surface to top of leaf canopy.*—About 29.5 cm.

*Plant width.*—About 58 cm.

*Leaves.*—Arrangement: Simple. Length: Petiole to apex: About 16 cm. Base to apex: About 22 cm. Width: About 14.5 cm. Shape: Oblique, ovate, asymmetrical. Apex: Acute. Base: Slightly overlapping cordate. Margin: Pectinate; irregularly undulate. Texture: Leathery, rugose; pubescence on lower surface veins. Color: Young foliage, upper surface: Margin: 200A. Central venal areas: Sharply defined velvet sheen darker than 200A. Blade: Metallic 53C to 185B merging with iridescent 186C to 186D and 192B. Antemarginal: Patches of 146A; veins reticulate, 185D. Young foliage, lower surface: Margin: 183A to darker than 187A. Central venal areas: Close to 183A. Background: 148C. Mature, fully expanded, foliage, upper surface: Margin: Dark brown, 200A, close to 202A. Central venal areas: Sharply defined velvety 200A to close to 202A. Blade to margin: Solid metallic, close to 46A; unevenly outlined with 192C and antemarginal splotches of 146A. Veins: 200B; outwardly becoming 185D. Mature, fully expanded, foliage, lower surface: Margin: Darker than 183A. Central venal area: Darker than 183A. Background: 148C. Veins: 183A; reticulate.

*Petioles.*—Length: About 17 cm. Diameter: About 7 mm. Shape: Longitudinally grooved. Texture: Pubescent. Color: 178A.

*Stipules.*—Length: About 15 mm. Diameter at base: About 8.5 mm. Shape: Subulate, deltoid. Color: Close to 179A.

Flower description:

*Flowering habit.*—Male flowers, single with one whorl of four tepals. Female flowers, semi-double with three tepals interior to outer whorl of five tepals. Usually about four or five flowers per cyme. Flowers persistent.

*Natural flowering season.*—Plants will flower continuously, but typically plants flower more abundantly during the spring and summer.

*Flowers.*—Shape: Rounded; somewhat cup-shaped. Diameter: About 2.5 cm. Depth (height): About 1.5 cm. Aspect: Drooping about 45° from vertical. Fragrance: None.

*Flower buds.*—Shape: Ovoid; bulbous with marginal lip. Length: About 11.5 mm. Diameter: About 7 mm. Color: 44C; lip, 43C.

*Tepals.*—Arrangement: Rosette. Length: About 1.5 cm. Width: About 1.2 cm. Shape: Ovate with obtuse apex. Margin: Entire. Texture: Smooth, waxy; iridescent, translucent. Color: When opening, upper surface: 48C. When opening, lower surface: 48C. Fully opened, upper surface: 55C. Fully opened, lower surface: 55D.

*Peduncles.*—Angle: About 30° from vertical. Length: About 2.5 cm. Diameter: About 1.5 mm. Strength: Firm. Texture: Smooth, waxy. Color: 178A.

*Pedicels.*—Angle: About 35° from vertical. Length: About 6 mm. Diameter: About 1 mm. Strength: Moderate. Texture: Smooth, waxy. Color: 179A.

*Reproductive organs.*—Male flowers: Stamen quantity: About 90, globose mass. Anther shape: Rhomboidal; lower sides curved inwardly. Anther length: About 2 mm. Filament length: About 1 mm. Anther color: 15A Pollen: Not observed. Female flowers: Pistil length: About 2.2 cm. Stigma shape: Funnel; bilobate. Stigma color: 25A. Ovary: Inferior, three-winged; one large top wing and two lower wings.

Disease resistance: Resistance to diseases common to Rex Begonia has not been determined.

Seed production: Seed production has not been observed.

It is claimed:

1. A new and distinct cultivar of Rex Begonia plant named 'Omaha Beefsteak', as illustrated and described.

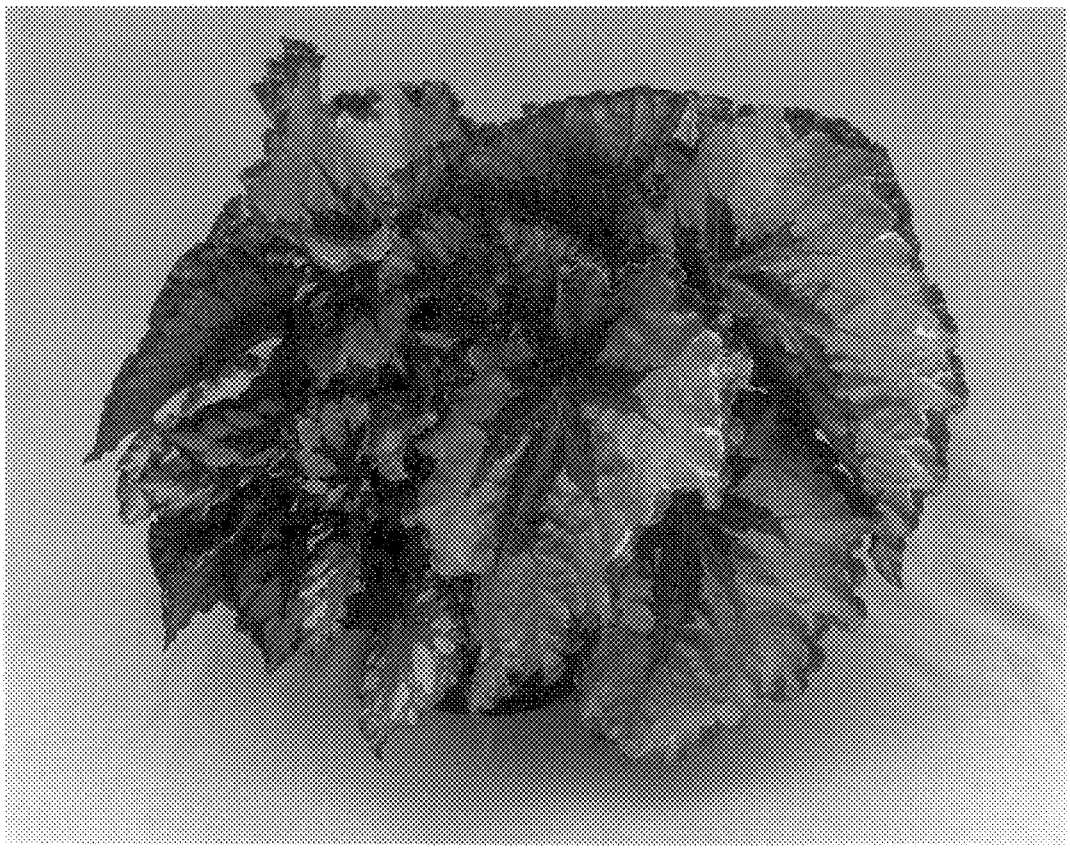

* * * * *